United States Patent [19]
Schervinsky

[11] Patent Number: 5,891,166
[45] Date of Patent: Apr. 6, 1999

[54] SURGICAL SUTURE HAVING AN ULTRASONICALLY FORMED TIP, AND APPARATUS AND METHOD FOR MAKING SAME

[75] Inventor: Semyon Schervinsky, Whitehouse Station, N.J.

[73] Assignee: Ethicon, Inc., Somerville, N.J.

[21] Appl. No.: 739,561

[22] Filed: Oct. 30, 1996

[51] Int. Cl.⁶ .................................................. A61B 17/04
[52] U.S. Cl. ........................... 606/228; 606/230; 606/231
[58] Field of Search .................................... 606/228, 230, 606/231

[56] References Cited

U.S. PATENT DOCUMENTS

| | | |
|---|---|---|
| 1,492,821 | 5/1924 | Weinbach . |
| 1,665,216 | 4/1928 | Morton et al. . |
| 2,173,789 | 9/1939 | Nikles et al. . |
| 2,803,109 | 8/1957 | Stoddard . |
| 3,165,958 | 1/1965 | Anderson et al. . |
| 3,317,924 | 5/1967 | Le Veen et al. . |
| 3,376,698 | 4/1968 | Whittaker . |
| 3,388,030 | 6/1968 | Estes et al. . |
| 3,449,549 | 6/1969 | Isobe et al. . |
| 3,479,670 | 11/1969 | Medell . |
| 3,564,958 | 2/1971 | Richter . |
| 3,642,010 | 2/1972 | Kuris . |
| 3,657,056 | 4/1972 | Winston et al. ......................... 156/580 |
| 3,736,646 | 6/1973 | Schmitt et al. . |
| 3,807,270 | 4/1974 | Wirz . |
| 3,835,912 | 9/1974 | Kristensen et al. . |
| 3,890,975 | 6/1975 | McGregor . |
| 3,943,933 | 3/1976 | Gertzman . |
| 3,949,756 | 4/1976 | Ace . |
| 3,980,177 | 9/1976 | McGregor . |
| 3,981,307 | 9/1976 | Borysko . |
| 4,014,648 | 3/1977 | Walsh et al. . |
| 4,041,814 | 8/1977 | High . |
| 4,075,046 | 2/1978 | MacDonald ............................ 156/73.1 |
| 4,173,311 | 11/1979 | Lucke . |
| 4,358,976 | 11/1982 | Alviti . |
| 4,377,427 | 3/1983 | Francois ................................. 156/73.2 |
| 4,460,820 | 7/1984 | Matsumoto et al. . |
| 4,470,941 | 9/1984 | Kurtz . |
| 4,510,934 | 4/1985 | Batra . |
| 4,669,474 | 6/1987 | Barrows . |
| 4,716,801 | 1/1988 | Spaller, Jr. . |
| 4,806,737 | 2/1989 | Coates . |
| 4,832,025 | 5/1989 | Coates . |
| 5,226,336 | 7/1993 | Coates . |
| 5,507,777 | 4/1996 | Kus et al. ............................... 606/224 |

FOREIGN PATENT DOCUMENTS

| | | |
|---|---|---|
| 0119287 | 9/1984 | European Pat. Off. . |
| 0950830 | 8/1982 | U.S.S.R. . |
| 0568675 | 4/1945 | United Kingdom . |
| 0950339 | 2/1962 | United Kingdom . |
| 0996908 | 6/1965 | United Kingdom . |

OTHER PUBLICATIONS

Prior Art Ultrasonic Suture Tipping Device and Process

*Primary Examiner*—Michael Buiz
*Assistant Examiner*—Tina T.D. Pham
*Attorney, Agent, or Firm*—Hal Brent Woodrow

[57] ABSTRACT

An apparatus and method for ultrasonically forming a surgical suture tip from a length of unfinished surgical suture material. The apparatus includes a first tipping die having a first face for contacting a portion of the length of unfinished surgical suture material. A second tipping die having a second face is also provided. At least one mechanical actuator is provided for moving the first face of the first tipping die toward the second face of the second tipping die. A second actuator vibrates at least one of the first and second tipping dies at an ultrasonic frequency of about 15 KHz to 70 KHz. The method of ultrasonically forming a suture tip comprises the positioning a surgical suture between the first face of the tipping die and the second face of the tipping die then vibrating the dies at an appropriate frequency.

4 Claims, 11 Drawing Sheets

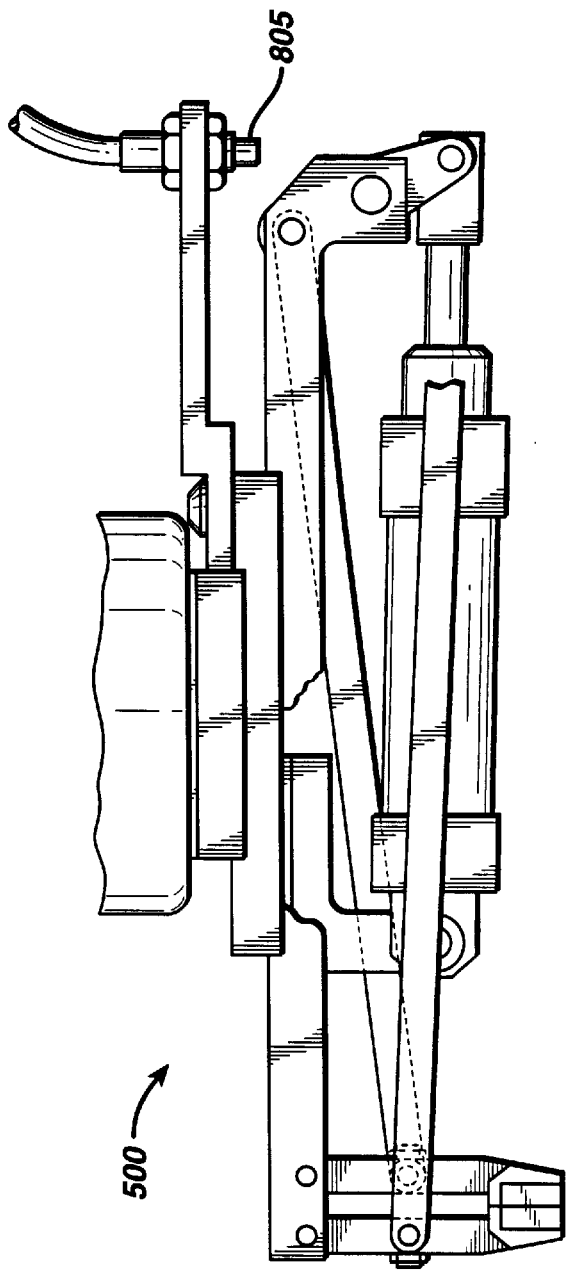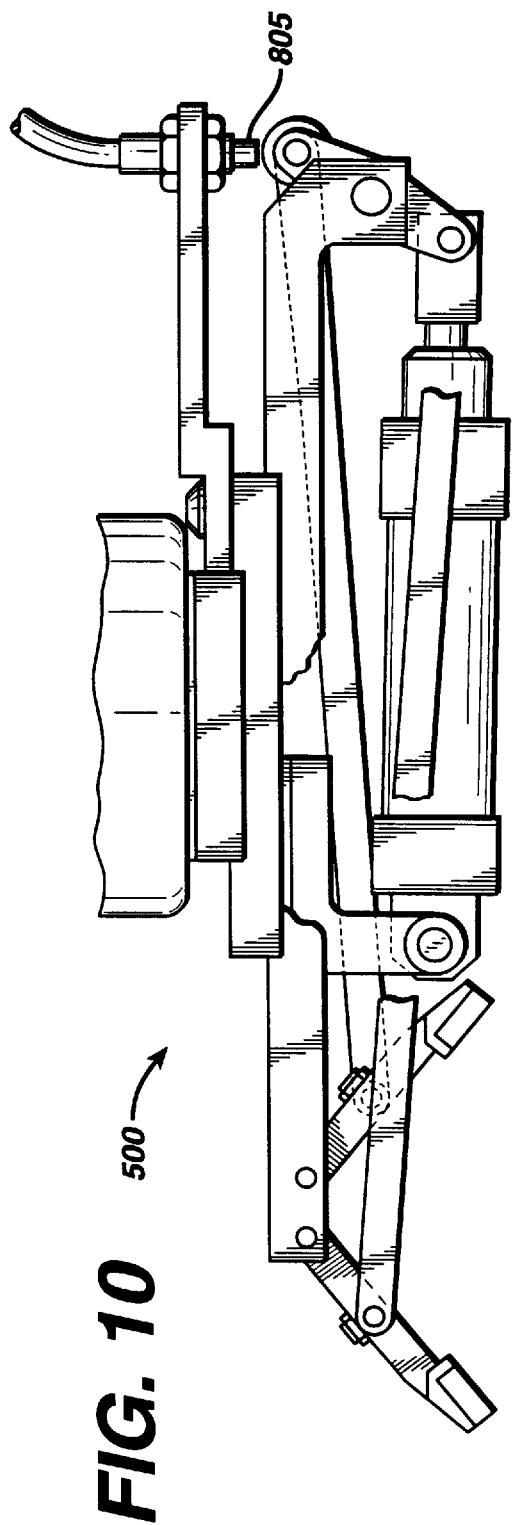

SURGICAL SUTURE HAVING AN ULTRASONICALLY FORMED TIP, AND APPARATUS AND METHOD FOR MAKING SAME

FIELD OF THE INVENTION

The present invention is directed to systems for processing strings and yarns. More particularly, the present invention is directed to automated systems for forming surgical suture tips through the use of ultrasonic welding.

BACKGROUND OF THE INVENTION

Various automated systems for forming and cutting surgical suture tips exist or are known in the art. In one such machine, means for simultaneously advancing in parallel at least six separate strands of suture material, and six independent tensioners for maintaining respective parallel portions of each of the six strands at a preset tension are provided. Once a predetermined length of suture material has been advanced by the advancing means, a horizontal heater bar (positioned perpendicular to the six suture strands) is actuated by an electronically controlled solenoid which moves a planar heater bar into contact with one side of the suture strands for a predetermined dwell time. Once the predetermined dwell time has elapsed, the solenoid retracts the heater bar to its original position, and the heat exposed (or heat-stiffened) section of suture material is advanced to a cutting station. At the cutting station, the heat-stiffened section of suture material is cut at its midpoint, thereby producing a suture with two stiffened ends. Other mechanisms for forming and cutting surgical suture tips are shown in U.S. Pat. Nos. 4,832,025, 4,806,737 and 5,226,336 to Coates. The system described in the Coates patents uses convective or non-contact heating to form suture tips.

Known systems for forming and cutting surgical suture tips suffer from several drawbacks. First, such systems typically use heat to stiffen the surgical suture tips. Since the unfinished surgical suture material used by such systems is often coated, the heat applied during the tipping process may melt the coating. Once it has melted, the coating from the unfinished surgical suture material often adheres to the tipping machine, thereby compromising the machine's performance. Another drawback of known systems for forming and cutting surgical suture tips is that such systems typically produce a suture tip which lacks a substantially uniform cross-section. In addition, such systems are undesirable in that they typically cut the suture tip in an imprecise manner, thereby leaving a cut end which may be irregular or distorted in shape. From a manufacturing standpoint, suture tips having non-uniform cross-sections and/or irregular or distorted cut ends are undesirable because, among other things, such sutures are difficult to insert into needles. Finally, known systems which use heat to stiffen surgical suture tips are undesirable because such systems cannot be used with sutures formed from silk.

It is therefore an object of the present invention to provide a system for forming surgical suture tips which system does not use heat in forming the suture tips and which may be used to fuse silk.

It is a further object of the present invention to provide a surgical suture having a welded core which facilitates the easy insertion of the suture tip into a needle.

It is a further object of the present invention to provide an automated system and method for manufacturing surgical sutures having tips with welded cores.

It is a still further object of the present invention to provide an automated system and method for making surgical sutures with tips having precisely cut ends.

These and other objects and advantages of the invention will become more fully apparent from the description and claims which follow or may be learned by the practice of the invention.

SUMMARY OF THE INVENTION

The present invention is directed to a multifilament surgical suture having a body portion and a tip portion which is adjacent to the body portion. The surgical suture is formed of a plurality of filaments. The tip portion has a tip length, a tip cross-section perpendicular to the tip length, and a tip core positioned at a center of the tip cross-section and along the tip length. The filaments positioned at the tip core are ultrasonically fused together.

In accordance with a further aspect, the present invention is directed to an apparatus for ultrasonically forming a surgical suture tip from a length of unfinished surgical suture material. The apparatus includes a first tipping die having a first face for contacting a portion of the length of unfinished surgical suture material. A second tipping die having a second face is also provided. At least one mechanical actuator is provided for moving the first face of the first tipping die toward the second face of the second tipping die. A second actuator vibrates at least one of the first and second tipping dies at an ultrasonic frequency of about 15 KHz to 70 KHz.

In accordance with a still further aspect, the present invention is directed to a method for ultrasonically forming a surgical suture tip from a length of unfinished surgical suture material. The length of unfinished surgical suture material is positioned at a location between a first face of a first tipping die and a second face of a second tipping die. After the positioning step, the surgical suture tip is formed by vibrating at least one of the first and second tipping dies at an ultrasonic frequency of about 15 KHz to 70 KHz.

BRIEF DESCRIPTION OF THE DRAWINGS

In order that the manner in which the above-recited and other advantages and objects of the invention are obtained and can be appreciated, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode thereof will be described and explained with additional specificity and detail through the use of the accompanying drawings.

FIG. 9 is a cross-sectional view of a moving clamp shown in its closed state for grasping and advancing surgical suture material, in accordance with a preferred embodiment of the present invention.

FIG. 10 is a cross-sectional view showing the moving clamp of FIG. 9 in its open state, in accordance with a preferred embodiment of the present invention.

DETAILED DESCRIPTION OF THE INVENTION

Overall System Operation

Figure 1:
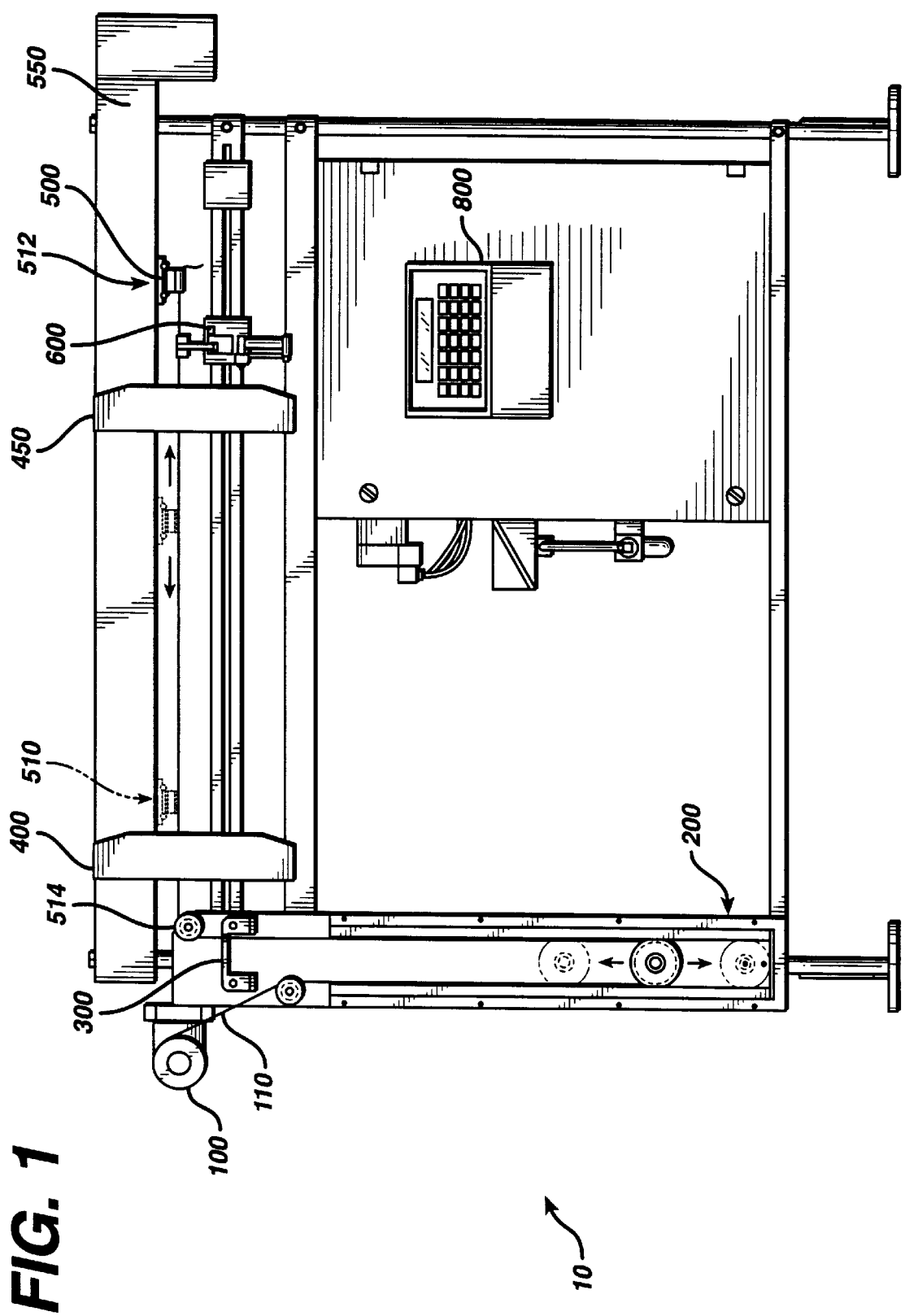
FIG. 1 is a schematic diagram showing a machine for ultrasonically forming and cutting surgical sutures, in accordance with a preferred embodiment of the present invention.

Referring now to FIG. 1, there is shown a schematic diagram showing a machine 10 for ultrasonically forming and cutting surgical sutures, in accordance with a preferred embodiment of the present invention. A continuous length of unfinished surgical suture material 110 is supplied to machine 10 from a supply spool 100 having unfinished surgical suture material 110 wound thereon. Unfinished surgical suture material 110 from supply spool 100 is initially advanced through a tensioning assembly 200 for creating a tension in the unfinished surgical suture material, and then through a knot detector system 300 for detecting whether a knot is present in any unfinished surgical suture material 110 passing through knot detector system 300. After passing through the knot detector system 300, the unfinished surgical suture material is advanced to a tipping station 400, where a predetermined length of the unfinished surgical suture material 110 is ultrasonically formed into a length of surgical suture tip material. After the ultrasonically formed surgical suture tip material is formed in station 400, the suture tip material is advanced to a cutting station 450 (e.g., an automated scissor or guillotine cutter) where the suture tip material is cut, thereby yielding a finished surgical suture having a body portion formed of unfinished surgical suture material 110 and an ultrasonically formed tip portion terminating with a cut end.

As explained more fully below, the unfinished surgical suture material 110 from supply spool 100 is advanced through machine 10 by a moving clamp 500 which is coupled to a linear actuator 550 for driving the moving clamp 500 between a starting or home position 510 on one side of the cutting station 450 and an end position 512 on the other side of the cutting station 450. Moving clamp 500 has a grasping (or closed) state shown in FIG. 9, and a non-grasping (or open) state shown in FIG. 10. In accordance with instructions received from a controller 800, the moving clamp 500 selectively grasps and pulls the unfinished surgical suture material 110 through machine 10 in order to facilitate the manufacture of the finished surgical sutures. In addition to advancing unfinished surgical suture material through the machine, the moving clamp 500 functions to initially position and align the unfinished surgical suture material 110 within the tipping station 400.

Figure 11:
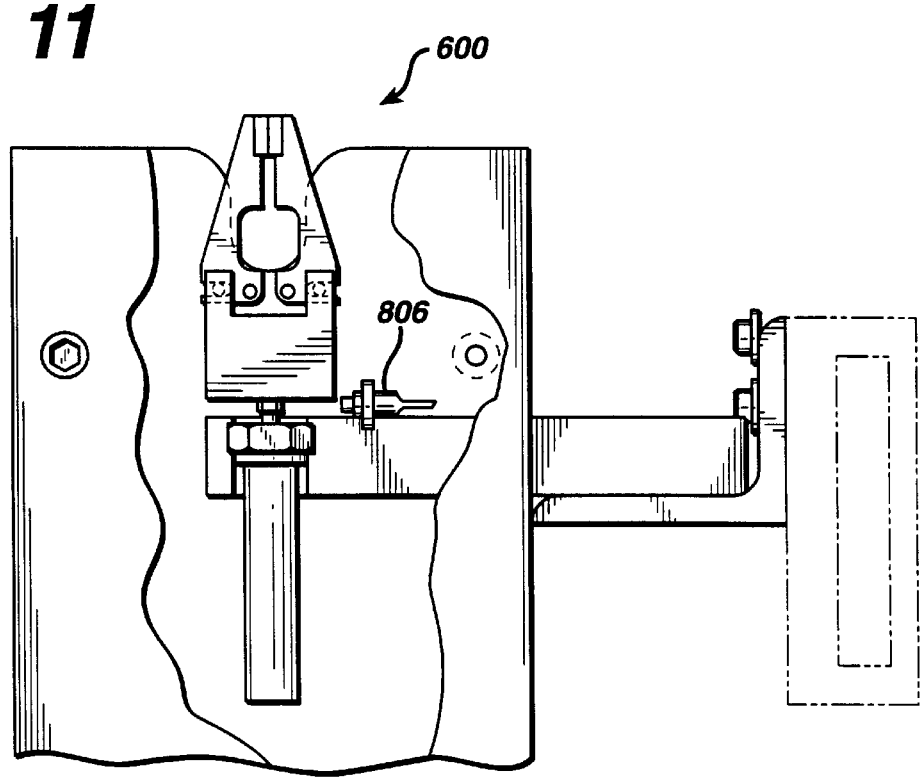
FIG. 11 is a cross-sectional view of a stationary clamp shown in its closed state for grasping surgical suture material, in accordance with a preferred embodiment of the present invention.
Figure 12:
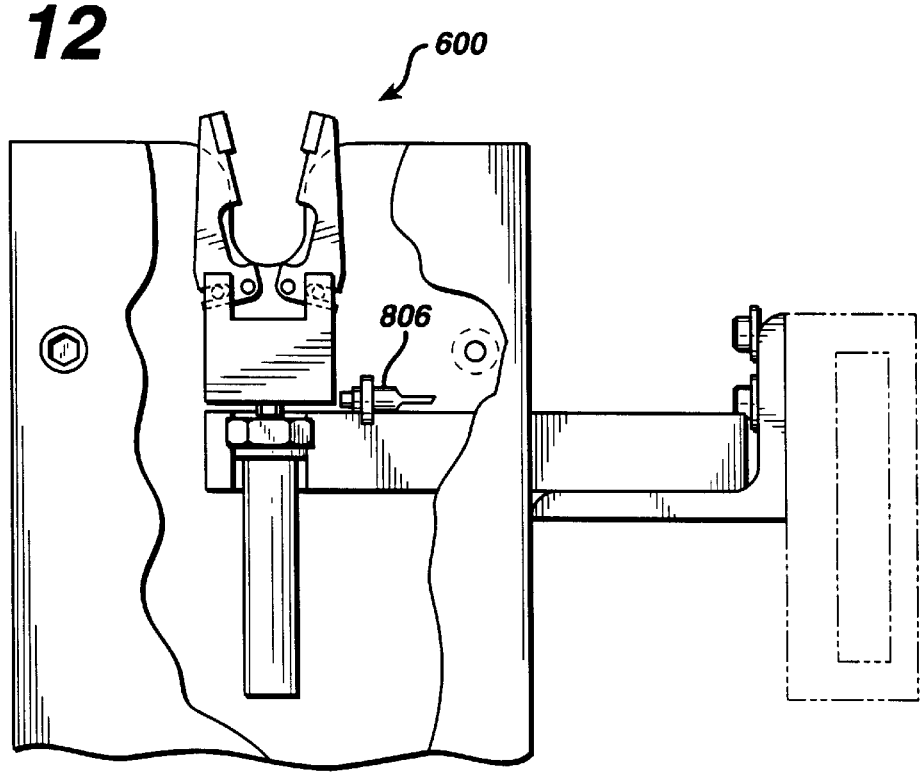
FIG. 12 is a cross-sectional view showing the stationary clamp of FIG. 11 in its open state, in accordance with a preferred embodiment of the present invention.

During operation of the machine 10, the moving clamp 500 initially grasps or closes on the unfinished surgical suture material 110 at the home position 510. Next, while the moving clamp 500 remains in its grasping or closed state, the linear actuator 550 drives the moving clamp 500 from its home position 510 to the end position 512. As the linear actuator 550 drives moving clamp 500 from its home position 510 to its position 512, the moving clamp 500 pulls a length of the unfinished surgical suture material 110 through the station 400 and through a stationary clamp 600 positioned adjacent to the end position 512. Like the moving clamp 500, the stationary clamp 600 has a grasping (or closed) state which is shown in FIG. 11, and a non-grasping (or open) state shown in FIG. 12. As the linear actuator 550 drives the moving clamp 500 from home position 510 to end position 512, the stationary clamp 600 is in its open state. After the moving clamp reaches its end position 512, the stationary clamp 600 grasps or closes on the unfinished surgical suture material 110 positioned within the stationary clamp 600. The positions of cutting station 450 and stationary clamp 600 along the length of machine 10 may be adjusted in order to facilitate the creation of sutures with different lengths.

Figure 2:
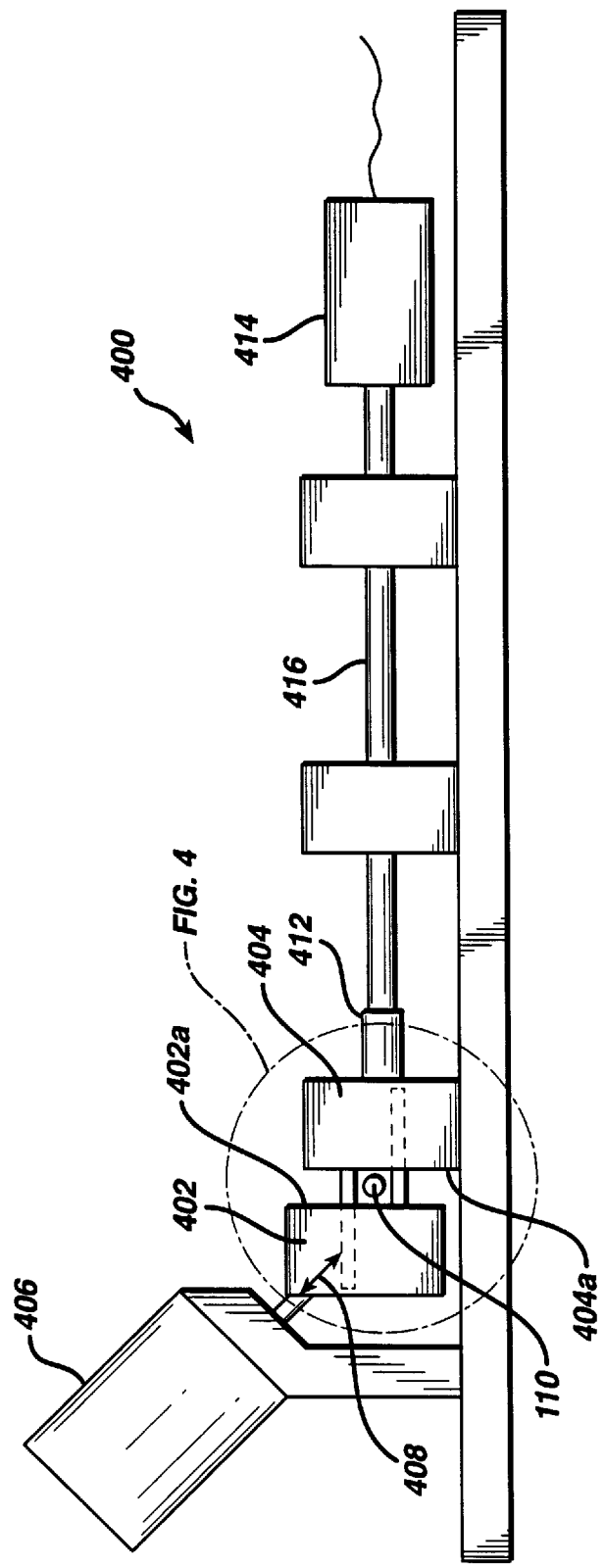
FIG. 2 is a side view of a suture tipping station formed from a pair of opposing tipping dies one of which is in its retracted position, in accordance with a preferred embodiment the present invention.
Figure 3:
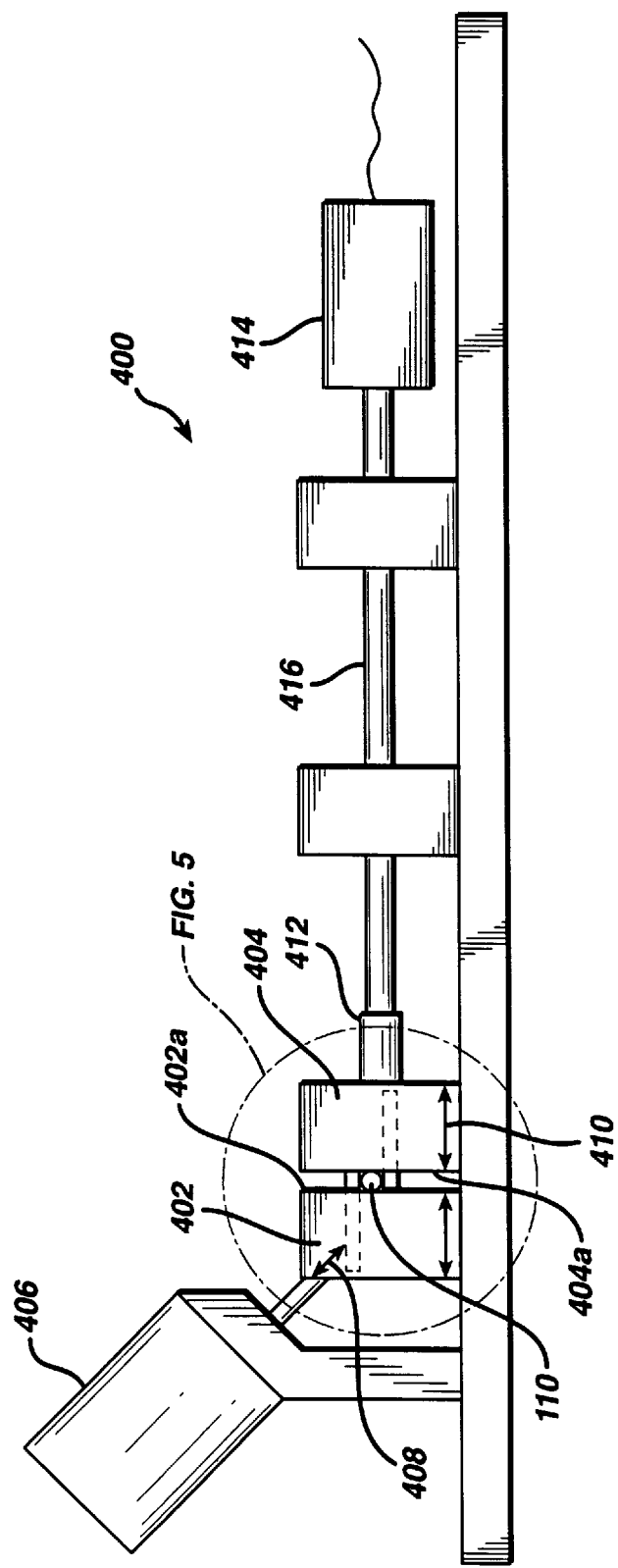
FIG. 3 is a side view of the suture tipping station of FIG. 2, wherein one of the tipping dies in the station is in its extended position.
Figure 4:
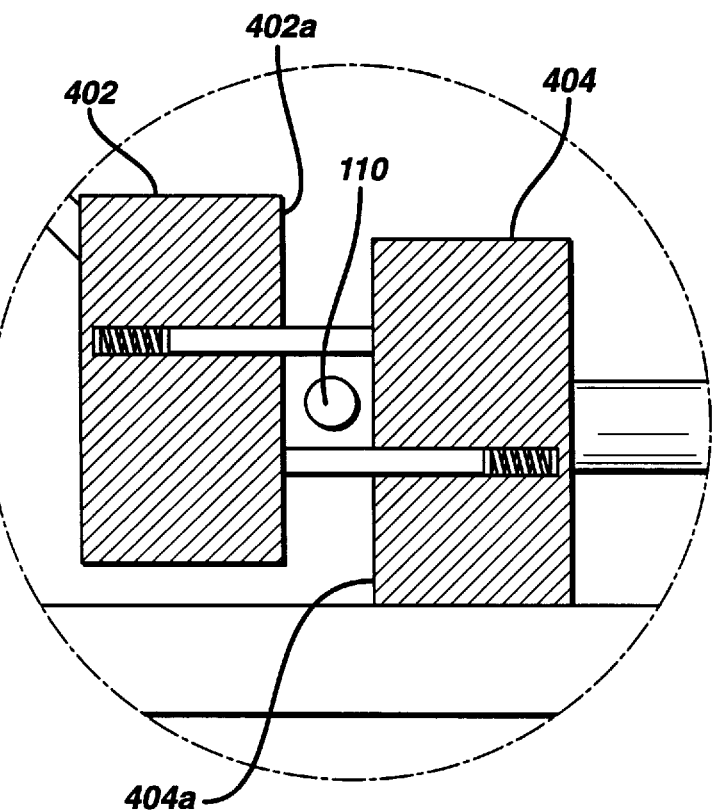
FIG. 4 is an enlarged view of a portion of the suture tipping station shown in FIG. 2.
Figure 5:
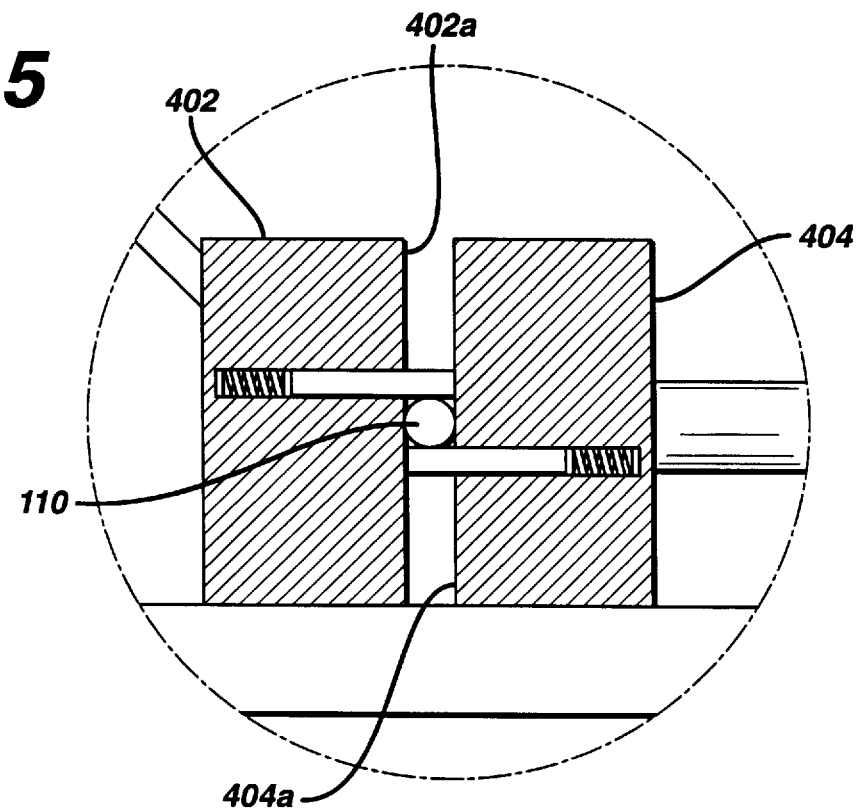
FIG. 5 is an enlarged view of a portion of the suture tipping station shown in FIG. 3.

As illustrated in FIGS. 2–3, the combined tipping and cutting station 400 includes a pair of opposing tipping dies 402, 404. The tipping die 402 has both an open state (shown in FIG. 2) and a closed state (shown in FIG. 3). When, as described above, the linear actuator 550 drives the moving clamp 500 from home position 510 to end position 512, the tipping die 402 in station 400 is in its open position. After the moving clamp reaches its end position 512 and the stationary clamp 600 has grasped or closed on the unfinished surgical suture material 110 positioned within the stationary clamp 600, the tipping die 402 moves from its open (or retracted) state to its closed (or extended) state in order to facilitate the ultrasonic forming of a predetermined length of surgical suture tip material. As described in greater detail below in connection with FIGS. 2–5, while the tipping die 402 is in its closed state, at least one of the tipping dies 402, 404 vibrates at an ultrasonic frequency in order to form a length of surgical suture tip material. After the tipping die 402 has been in its closed state for a predetermined period of dwell time (i.e., weld time plus hold time), tipping die 402 moves from its closed to its open state, thereby yielding a length of tipped surgical suture material positioned between dies 402, 404. While this length of tipped surgical suture material remains positioned between dies 402, 404, a further length of tipped surgical suture material (previously tipped by station 400) which is positioned within cutting station 450 is severed by station 450, thereby yielding a tipped surgical suture with a cut end.

While the surgical suture material positioned at station 400 is being tipped, the moving clamp 500 opens and releases the surgical suture material within its grasp and, with the tipping die 402 still in its closed state, the linear actuator 550 drives the moving clamp 500 from its end position 512 to its home position 510 where the moving clamp closes on a next piece of unfinished surgical suture material 110. Next, after the tipping of the surgical suture material at station 400 is completed and the tipping die 402 is in its open state, the suture material at station 450 is cut. Thereafter, the stationary clamp 600 releases the surgical suture material within its grasp (i.e., a finished surgical suture with a cut tip), the linear actuator 550 drives the closed moving clamp back to its end position 512, and the process described above is then preferably repeated in order to manufacture further finished surgical sutures. Since the tensioning assembly 200 exerts a tensioning force on the surgical suture material 110 positioned within machine 10, it is important for the moving clamp 500 to grasp or close on the surgical suture material prior to the time that the stationary clamp 600 opens, in order to prevent the tensioning assembly 200 from pulling the trailing end of the surgical suture material cut by station 450 in a reverse direction when the tipped surgical suture material is severed by station 450.

The unfinished surgical suture material 110 used in machine 10 for manufacturing the finished sutures may consist of any thermoplastic braided suture material such as, for example, a polyester braided suture material, or a polyamide or polyolyfin suture material. In addition, the unfinished surgical suture material 110 used in machine 10 may consist of silk or linen material, in which case, machine 10 may be used to ultrasonically fuse silk or linen tips. Alternatively, the unfinished surgical suture material 110 used in machine 10 may consist of nylon material, in which case, machine 10 may be used to ultrasonically fuse nylon tips. In a preferred embodiment of the present invention described more fully below, the unfinished surgical suture material 110 used in machine 10 is a braided suture material formed of a polyethylene terephthalate, such as that sold by Ethicon, Inc. under the trademark Ethibond® Excel®. In a preferred embodiment, a Simatic model TI1435 controller manufactured by Siemens is used to implement controller 800. An operator interface is preferably coupled to the controller 800.

Operation of Tipping Dies

As mentioned above, after the moving clamp 500 has reached its end position 512, the tipping dies 402, 404 in the tipping station 400 operate to ultrasonically form a predetermined length of surgical suture tip material from the unfinished surgical suture material 110 positioned within the station 400. During the operation of the tipping dies 402, 404, the unfinished surgical suture material 110 is suspended in an aligned and fixed positioned within station 400 by the stationary clamp 600 which is positioned on one side of station 400, and by the pulley 514 which is positioned on an opposing side of station 400. In addition, during the operation of the tipping dies 402, 404, the unfinished surgical suture material 110 suspended within station 400 is maintained at a preset tension by tensioning system 200.

FIGS. 2 and 3 show two views of the tipping station 400. Each of the views illustrates the position of the tipping dies 402, 404 at a particular point during a suture tipping cycle. Referring now specifically to FIG. 2, there is shown a side view of station 400, wherein the tipping die 402 is in its retracted or open position. FIG. 2 shows the position of tipping die 402 when the moving clamp 500 first reaches its end position 512. After the moving clamp 500 has reached its end position 512, a cylinder 406 (controlled by controller 800) drives the tipping die 402 from its retracted to its extended position. In moving the tipping die 402 between its retracted and extended positions, cylinder 406 drives tipping die 402 along the axis indicated by arrows 408. FIG. 3 shows the position of the tipping die 402 after the cylinder 406 has moved tipping die 402 to its extended position. As the tipping die 402 is moved to its extended position, a cross-sectional portion of the suture material 110 suspended within station 400 is contacted by face 402a of tipping die 402 and face 404a of tipping die 404. In a preferred embodiment of the present invention, the cylinder 406 causes tipping die faces 402a and 404a to apply pressure to (or squeeze) the outer surfaces of the suture material 110 positioned between dies 402 and 404. In this preferred embodiment, about 25 PSI of pressure is applied to the outer surfaces of the suture material when die faces 402a and 404a "close-on" or squeeze the suture material positioned in station 400.

Figure 6:
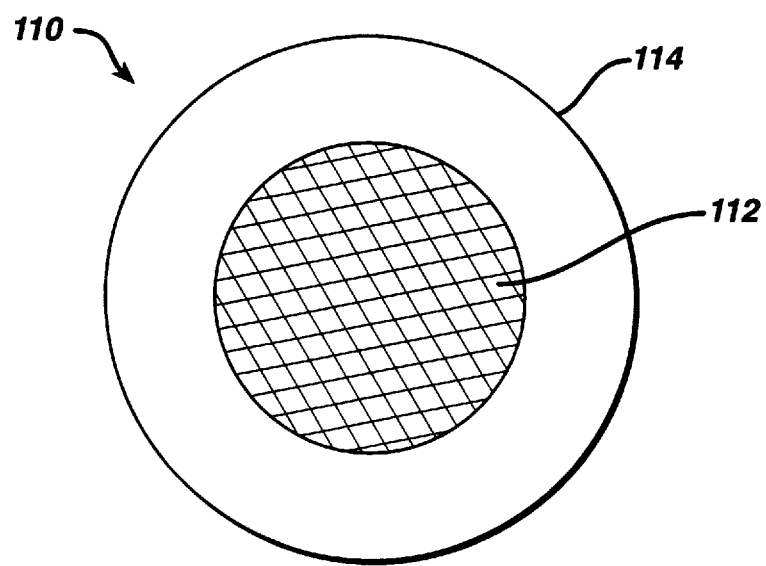
FIG. 6 shows a cross-sectional view of a length of surgical suture material which has been ultrasonically fused at its core, in accordance with a preferred embodiment of the present invention.

After faces 402a and 404a have been brought together and the tipping dies 402, 404 have "closed on" the unfinished surgical suture material 110 as shown in FIG. 3, one or both of the tipping dies 402, 404 vibrate at an ultrasonic frequency for a predetermined weld time in order to form a suture tip. In the preferred embodiment, tipping die 402 remains fixed in position during a dwell time (i.e., a weld time followed by a hold time) when the tipping dies 402, 404 have closed-on the unfinished surgical suture material 110, and an ultrasonic horn 412 which is connected to tipping die 404 vibrates tipping die 404 along the axis 410 at a frequency of 15 KHz to 70 KHz and an amplitude of 0.0001 to 0.010 inches for about 0.050 to 10.0 seconds in order to form the suture tip. In a still further preferred embodiment, horn 412 vibrates tipping die 404 at a frequency of 20 KHz to 40 KHz at an amplitude of 0.004 inches for 200 ms during the suture tipping step. During the dwell time when the tipping dies 402, 404 have closed-on the unfinished surgical suture material 110, the vibrating of tipping die 404 against tipping die 402 causes filaments within the interior or core 112 (shown in FIG. 6) of the unfinished surgical suture material 110 (as well as filaments on the exterior surface 114 of the suture material) to fuse or weld together, thereby forming a length of surgical suture tip material between dies 402, 404. Thereafter, at the end of the dwell time, the cylinder 406 opens the tipping die 402 by bringing it back to its initial retracted position. In the preferred embodiment, a transducer 414 which is coupled to horn 412 by a booster 416 is used for vibrating horn 412. Booster 416 functions to control the amplitude of the ultrasonic vibrations. A finished surgical suture formed with an ultrasonically fused suture tip as described above has been found to exhibit a tensile strength along the suture tip that is about 75% to 84% of the tensile strength of the body portion (i.e., the untipped portion) of the finished suture.

The tipping parameters used to form an ultrasonically fused tip vary depending upon the diameter of the unfinished suture material 110 being supplied to machine 10. Set forth in Table I below are the preferred tipping parameters used for ultrasonically forming tips on different sizes of an unfinished braided suture material formed of a polyethylene terephthalate, such as that sold by Ethicon, Inc. under the trademark Ethibond® Excel®. Also set forth in Table I below for each size suture is the preferred pressure to be applied to the exterior surfaces of the suture material by tipping dies 402, 404 when the tipping dies first "close-on" the unfinished suture material, the preferred frequency that tipping die 404 should vibrate during the ultrasonic tipping process, and the preferred dwell times during which the tipping dies 402, 404 should remain closed on (and vibrate against) the unfinished suture material 110 during the ultrasonic tipping process.

TABLE I

| SIZE | 0 | 2/0 | 3/0 | 4/0 | 5/0 |
| --- | --- | --- | --- | --- | --- |
| Tipping Die Pressure (in PSI) | 80 | 25 | 25 | 15 | 5 |
| Tipping Die Vibration Frequency (in KHz) | 15–70 | 15–70 | 15–70 | 15–70 | 15–70 |
| Tipping Die Weld Time (in seconds) | 0.900–10.0 | 0.400–5.0 | 0.100–5.0 | 0.025–2.0 | 0.025–2.0 |
| Tipping Die Hold Time (in seconds) | 0.100–0.500 | 0.100–0.500 | 0.100–0.500 | 0.100–0.500 | 0.100–0.500 |

Figure 7:
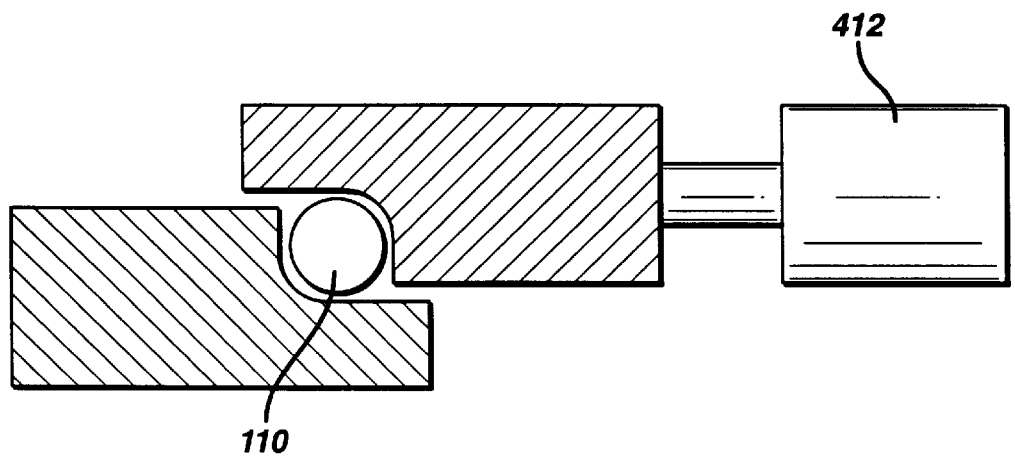
FIGS. 7 and 8 show side views of opposing tipping dies for ultrasonically forming surgical suture tips, in accordance with alternative preferred embodiments of the present invention.
Figure 8:
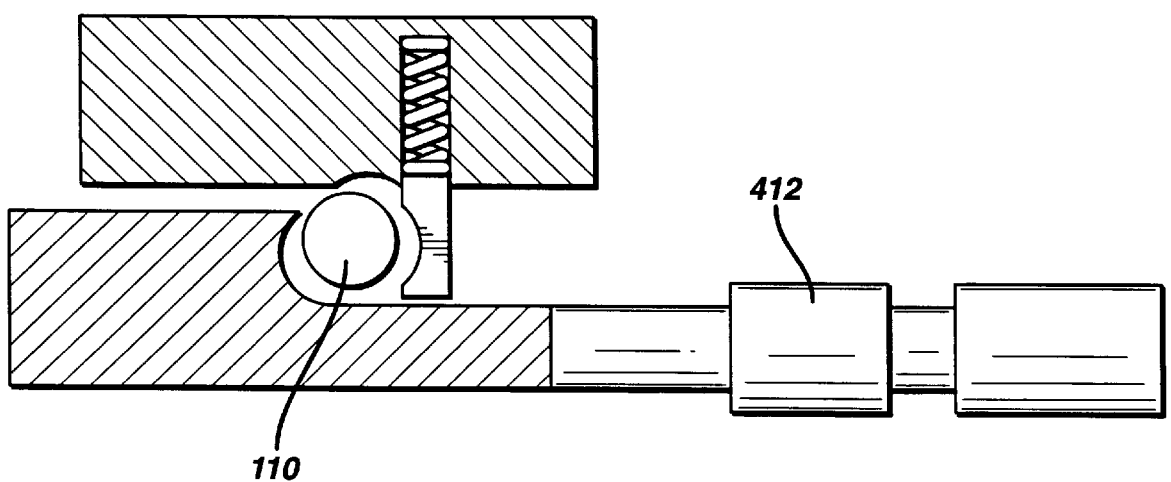

In the preferred embodiment of the present invention, tipping dies 402, 404 are made of steel, and are coated with a non-stick substance such as TiN, Teflon® or Nedox®, in order to facilitate the release of the suture material from the tipping dies 402, 404 when such dies are opened. Although in the preferred embodiment described above, the tipping dies 402 and 404 were a particular shape, it will be understood by those skilled in the art that tipping dies defining other shapes, such as those shown in FIGS. 7 and 8, may also be used to ultrasonically form suture tips in accordance with the present invention. Similarly, although the ultrasonically tipped suture shown in FIG. 6 has a circular cross-section, it will be understood by those skilled in the art that ultrasonically tipped sutures having cross-sections of other shapes (e.g., polygonal) may be formed in accordance with the present invention by varying the shape and orientation of the tipping dies employed.

Suture Tensioning System

Figure 13:
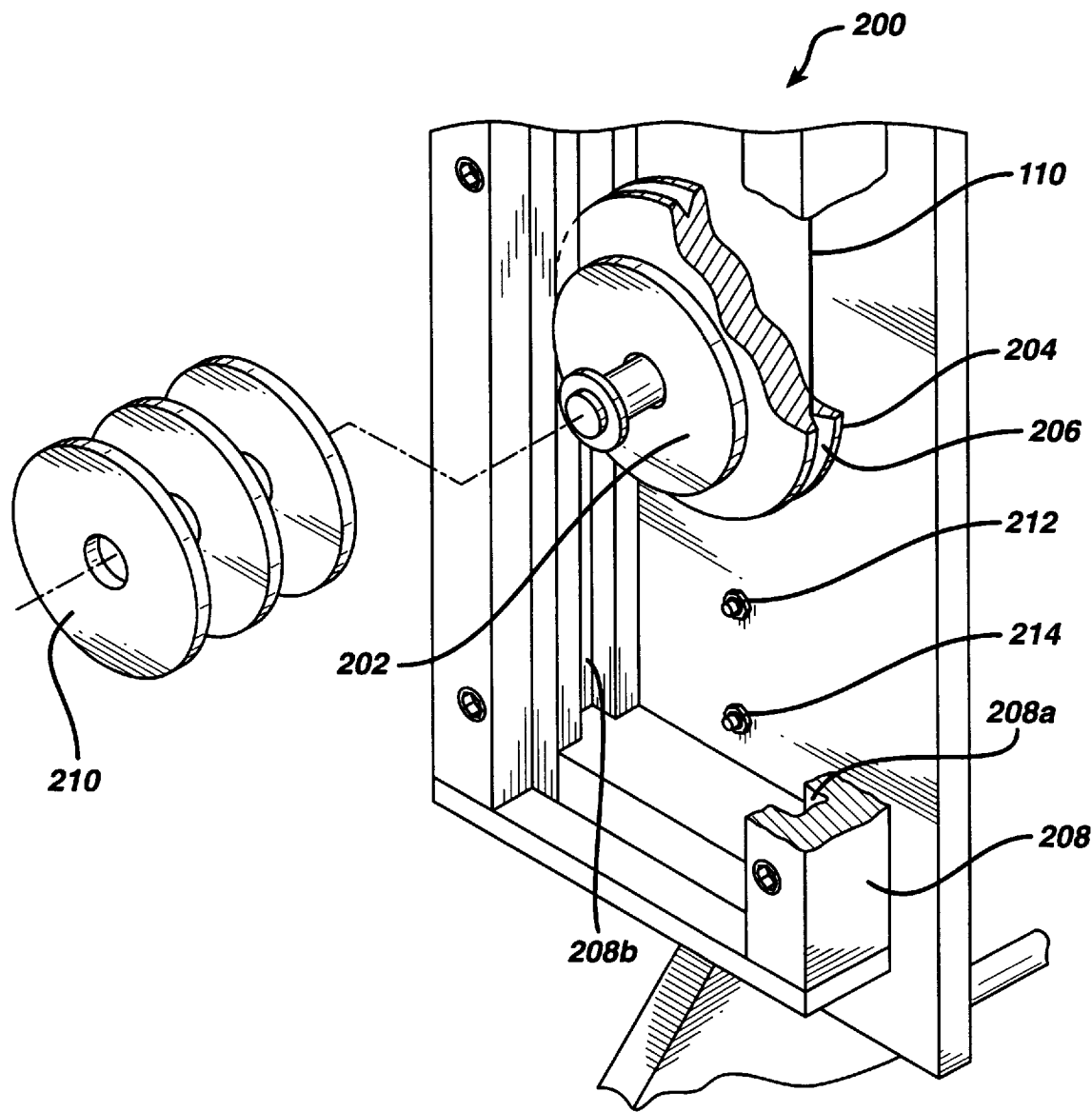
FIG. 13 is an isometric view of a system for tensioning a length of surgical suture material, in accordance with a preferred embodiment of the present invention.

Referring now to FIG. 13, there is shown an isometric view of the system 200 for tensioning a length of surgical suture material 110, in accordance with a preferred embodiment of the present invention. System 200 includes a tensioning spool 202 having a width, a weight and a circular perimeter 204 perpendicular to the width of the spool. The tensioning spool 202 has a groove 206 in its perimeter 204 for receiving the surgical suture material 110. Tensioning system 200 also includes a track 208 formed from a pair slots 208a, 208b extending in parallel along the length of the track 208. Track 208 and slots 208a, 208b are preferably positioned along a purely vertical axis, although, in alternate embodiments (not shown), track 208 and slots 208a, 208b may be aligned along an axis that includes both horizontal and vertical components. The slots 208a, 208b function to receive and guide the tensioning spool 202 along the length of track 208 during operation of system 200. The length of the track 208 is preferably aligned perpendicularly to the width of the tensioning spool 202.

During operation of the system 200, the tensioning spool 202 is suspended vertically within slots 208a, 208b by the surgical suture material 110. While the tensioning spool 202 is suspended vertically within slots 208a, 208b by the surgical suture material 110, the weight of the tensioning spool 202 exerts a corresponding tensioning force on the suture material 110 equal to the weight of spool 202. In order to vary the tension exerted on the suture material 110 during operation of system 200, additional weights 210 may be added or removed from a spool arm extending from the center of spool 202. The tension exerted on the suture material 110 during operation of system 200 preferably represents the minimum tension necessary to prevent the suture material 110 from getting "bunched-up" as it is pulled through machine 10 by moving clamp 500.

When the moving clamp 500 described above is in its grasping state and moves from its home position 510 to its end position 512, suture material 110 suspended in the slots 208a, 208b is drawn forwardly through station 400 of machine 10. As the suture material is drawn forwardly through the machine by the moving clamp 500, the tensioning spool 202 is pulled upwardly within slots 208a, 208b. However, regardless of the vertical position of the spool 202 within the slots 208a, 208b, the tension exerted on the suture material 110 by system 200 will be the constant and equal to the weight of spool 202. An optical sensor 212, coupled to controller 800, is provided for determining whether the pulling action of the moving clamp 500 has caused the spool 202 to be drawn upwardly within the track 208 past the height of the sensor 212. When optical sensor 212 detects that the tensioning spool 202 has been pulled upwardly past the location of the sensor 212, controller 800 causes a motor (not shown) coupled to the supply spool 100 to unwind unfinished surgical suture material 110 from the supply spool 100. As further unfinished surgical suture material 110 is unwound from the supply spool 100, the tensioning spool 202 moves downwardly within the track 208. In the preferred embodiment, controller 800 continues to unwind unfinished surgical suture material 110 from the supply spool 100 until the tensioning spool 202 falls below the level of optical sensor 212.

An optical sensor 214 is provided at the bottom of track 208 for determining whether there has been a break in the surgical suture material 110 or a loss of tension in the suture material within machine 10. Since, during normal operation, the tensioning spool 202 should not fall below the level of optical sensor 212, a break in suture material 110 or a loss of suture tension within machine 10 will be signaled by sensor 214 if the sensor determines that the tensioning spool 202 has fallen to the level of the sensor 214.

Knot Detection System

Figure 14:
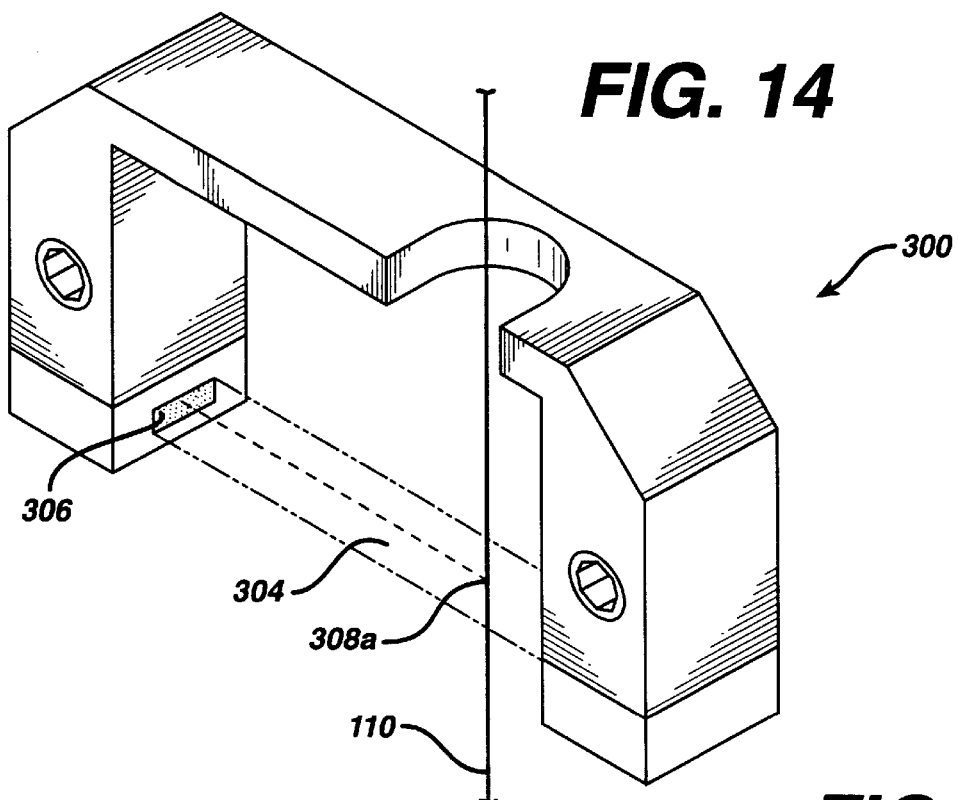
FIG. 14 is an isometric view of an optical detection system for detecting knots in surgical suture material passing through the system, in accordance with a preferred embodiment of the present invention.
Figure 16:
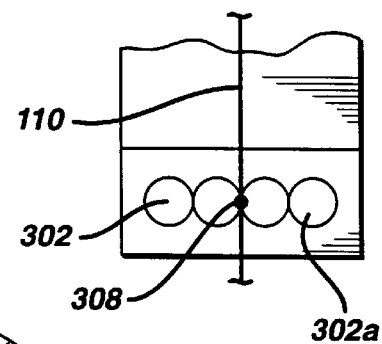
FIG. 16 is a cross-sectional view of FIG. 15, showing a knot positioned between the optical source and the optical detector of the knot detection system of FIG. 14, in accordance with a preferred embodiment of the present invention.
Figure 15:
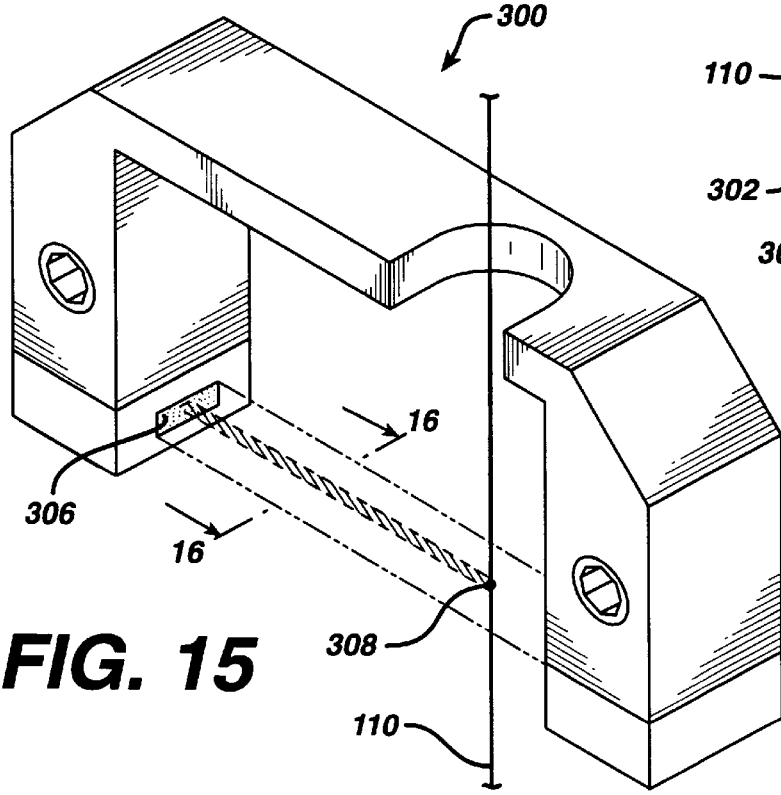
FIG. 15 is a further isometric view showing a knot positioned between the optical source and the optical detector of the knot detection system of FIG. 14, in accordance with a preferred embodiment of the present invention.

Referring now to FIGS. 14 and 15, there are shown two isometric views of an optical detection system 300 for detecting knots in surgical suture material 110 passing through system 300, in accordance with a preferred embodiment of the present invention. Knot detector system 300 includes an optical light source 302 for directing a plane of light 304 at an optical light detector 306 when surgical suture material 110 is positioned between the optical light source 302 and the optical light detector 306. The optical light source 302 is preferably formed of a plurality of optical fibers 302a having their terminating ends aligned along the optical plane 304. Controller 800 is coupled to an output of the optical light detector 306 for processing the signals output by detector 306 and determining whether a knot exists in the suture material 110 positioned between the light source 302 and light detector 306. More particularly, by comparing a magnitude of a shadow 308 cast on the optical light detector 306 by the suture material 110 against a predetermined threshold, controller 800 determines whether or not a knot exists in the suture material 110 positioned between the light source 302 and light detector 306. In a preferred embodiment, the predetermined threshold used in this comparison corresponds to a magnitude of a shadow 308a cast on the optical light detector 306 by an unknoted cross-section of suture material 110. In a still further preferred embodiment, controller 800 will determine that a knot exists in the suture material 110 passing through system 300 only if the magnitude of the shadow cast on light detector 306 by suture material 110 exceeds by at least 30% the magnitude of a shadow 308a cast on the optical light detector 306 by an unknoted cross-section of suture material 110.

Extended Length Suture Mode

Although, in the process described above, machine 10 was used to manufacture a finished surgical suture having a length that was less than length of the linear actuator 550, machine 10 may also be used in an extended length suture mode, described below, in order to make finished surgical sutures which are longer than linear actuator 550. During operation of the machine 10 in the extended length suture mode, the moving clamp 500 initially grasps or closes on the unfinished surgical suture material 110 at the home position 510. Next, while the moving clamp 500 remains in its grasping or closed state, the linear actuator 550 drives the moving clamp 500 from its home position 510 to the end position 512. As the linear actuator 550 drives moving clamp 500 from its home position 510 to its position 512, the moving clamp 500 pulls a length of the unfinished surgical suture material 110 through the tipping station 400, cutting station 450 and through the stationary clamp 600. After the moving clamp reaches its end position 512, the stationary clamp 600 grasps or closes on the unfinished surgical suture material 110 positioned within the stationary clamp 600. The moving clamp 500 then releases the unfinished surgical suture material 110 in its grasp. Next, while the moving clamp is in its open or non-grasping state, the linear actuator 550 drives the moving clamp 500 from its end position 512 to its home position 510, where the moving clamp 500 again grasps or closes on the unfinished surgical suture material 110 at the home position 510. After the moving clamp 500 grasps the unfinished surgical suture material 110 at the home position 510 for the second time, the stationary clamp 600 opens. Thereafter, while the moving clamp 500 remains in its grasping or closed state and the stationary clamp 600 remains in its open state, the linear actuator 550 again drives the moving clamp 500 from its home position 510 to the end position 512. After the moving clamp 500 reaches its end position 512 for the second time, the stationary clamp 600 again grasps or closes on the unfinished surgical suture material 110 positioned within the stationary clamp 600.

After the unfinished surgical suture material 110 has been "pulled twice" by the moving clamp 500 as described in the paragraph above, the dies 402, 404 in the tipping station 400 function as described above to ultrasonically form a length of surgical suture tip material positioned within the station 400. Following the cutting of this suture tip material at station 450, the stationary clamp 600 releases the surgical suture material within its grasp. As the stationary clamp opens and releases the previously grasped surgical suture material, a finished surgical suture having an ultrasonically formed and cut tip results. Since the moving clamp 500 pulled the suture material 110 two times consecutively before the tipping station 400 formed the suture tip, the resulting finished surgical suture produced by the extended length suture mode may have a length which is greater than the length of the linear actuator 550.

Continuous Process Using Circular Tipping Dies

Figure 18:
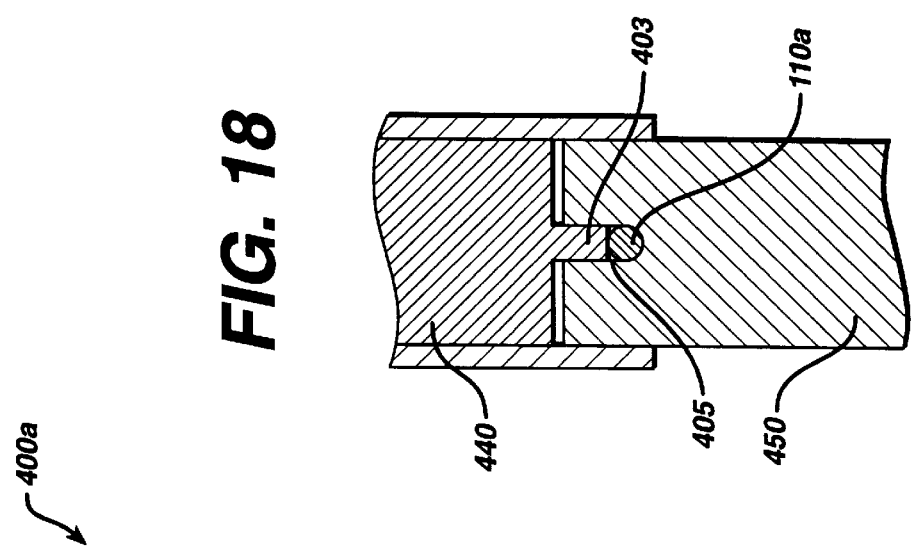
FIG. 18 is a cross-sectional view of the suture tipping station shown in FIG. 17.
Figure 17:
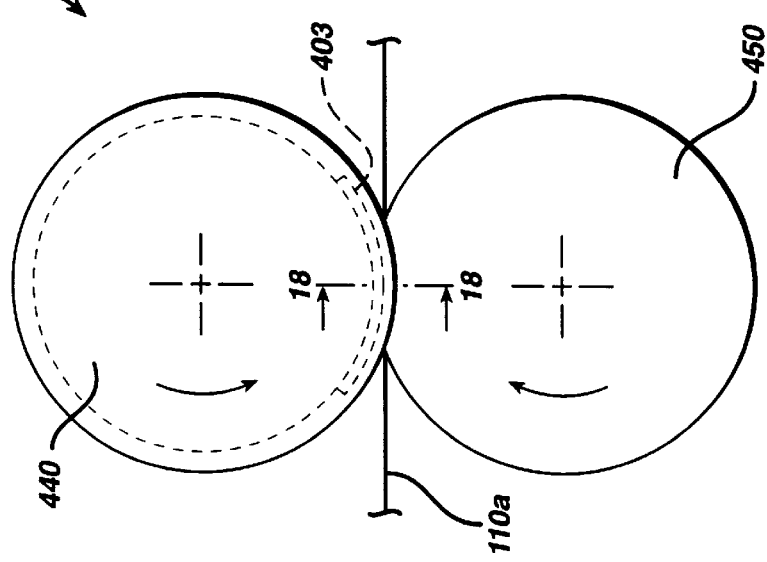
FIG. 17 is a side view of a suture tipping station formed of opposing circular tipping dies, in accordance with an alternative preferred embodiment of the present invention.

Referring now to FIGS. 17 and 18, there are shown side and cross-sectional views of an alternative suture tipping station 400a formed of opposing circular tipping dies 440, 450 for continuously tipping unfinished surgical suture material 110a, in accordance with an alternative preferred embodiment of the present invention. Tipping die 440 contains a notch 403 around a portion of its perimeter, and tipping die 450 contains a corresponding groove 405 positioned about its perimeter. In the preferred embodiment of station 400a, notch 403 is sized such that pressure is applied to the exterior surface of suture material 110a when suture material 110a is between notch 403 and the lower end of groove 405. Tipping dies 440, 450 are coupled to mechanical actuators (not shown) which continually rotate the dies 440, 450 in the direction of the arrows shown in FIG. 17. During rotation of the tipping dies 440, 450, an ultrasonic horn (also not shown) vibrates tipping die 440 against tipping die 450 at a frequency of 15 KHz to 70 KHz (and preferably 20 KHz to 40 KHz) and an amplitude of 0.0001 to 0.010 inches in order to continuously form suture tip material. Station 400a may be substituted for station 400 in FIG. 1, in order to configure machine 10 to continuously produce surgical sutures with ultrasonically formed tips, in accordance with the present invention.

Figure 19:
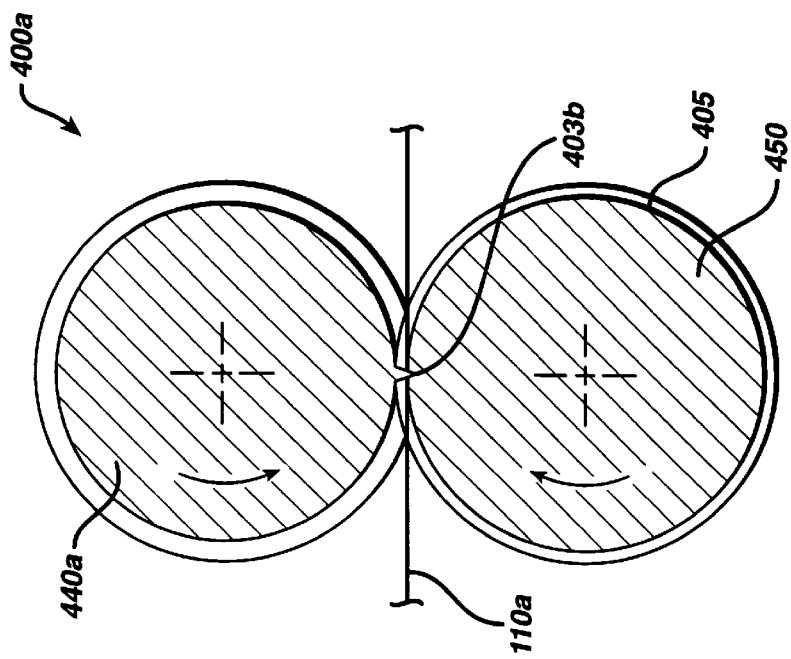
FIG. 19 is a side view of a suture tipping and cutting station formed of opposing circular tipping and cutting dies, in accordance with a further alternative preferred embodiment of the present invention.

Referring now to FIG. 19, there is shown a side view of a suture tipping and cutting station 400b formed of opposing circular tipping and cutting dies 440a, 450 for continuously tipping and cutting unfinished surgical suture material 110, in accordance with a further alternative preferred embodiment of the present invention. Die 440a is substantially the same as die 440, except that die 440a includes a cutting point 403b for cutting a suture tip end portion during the rotation of die 440a against 450. Station 400b functions substantially the same as station 400a, except that station 400b may be used to both form and cut suture tips in a continuous manner. Since the cutting performed by station 400b is accomplished using a cutting point 403b which vibrates at an ultrasonic frequency, a suture tip is simultaneously both cut and sealed by station 400b. In addition, the ultrasonic cutting action of point 403b yields a cut suture tip with a lead angle which facilitates the insertion of the cut suture tip into a drilled needle. Although in the preferred embodiment of station 400b, dies 440a and 450 function to both tip and cut surgical suture material 110, it will be understood by those skilled in the art that two separate pairs of circular dies may be employed in series to respectively perform the tipping and cutting operations.

Furthermore, it is to be understood that although the present invention has been described with reference to a preferred embodiment, various modifications, known to those skilled in the art, may be made to the structures and process steps presented herein without departing from the invention as recited in the several claims appended hereto.

What is claimed is:

1. An apparatus for ultrasonically forming a surgical suture tip from a length of unfinished surgical suture material, comprising:

(A) a tipping station having a first tipping die having a first face for contacting a portion of said length of said unfinished surgical suture material; a second tipping die having a second face at least one mechanical actuator for moving said first face of said first tipping die toward said second face of said second tipping die wherein said first and second tipping die faces contact and apply pressure to the outer surface of the unfinished suture material; and a second actuator for vibrating at least one of said first and second tipping dies at an ultrasonic frequency of about 15 kHz to 70 kHz;

(B) a cutting station for cutting said portion of said surgical suture;

(C) a moving clamp for advancing the surgical suture material from the tipping station to the cutting station; and (D) a stationary clamp for holding the suture in a stationary position, located adjacent to the cutting station.

2. The apparatus of claim 1, wherein said second actuator is provided for vibrating at least one of said first and second tipping dies at an amplitude of 0.0001 to 0.010 inches.

3. The apparatus of claim 2, wherein said second actuator is coupled to said second tipping die and is formed of an acoustic horn.

4. The apparatus of claim 1, wherein said at least one mechanical actuator is formed from a cylinder coupled to said first tipping die for moving said first tipping die from its open to its closed position.

* * * * *

UNITED STATES PATENT AND TRADEMARK OFFICE
CERTIFICATE OF CORRECTION

PATENT NO. : 5,891,166
DATED : April 6, 1999
INVENTOR(S) : Semyon Shchervinsky

It is certified that error appears in the above-indentified patent and that said Letters Patent is hereby corrected as shown below:

On the title page, Items [75] and [19],

Please delete "Schervinsky" and replace with ---Shchervinsky---.

Signed and Sealed this

Third Day of August, 1999

Attest:

Q. TODD DICKINSON

Attesting Officer

Acting Commissioner of Patents and Trademarks